United States Patent [19]
Kaartinen

[11] 3,979,503
[45] *Sept. 7, 1976

[54] METHOD AND APPARATUS FOR PROCESSING FLUID MATERIALS PARTICULARLY IN THE PREPARATION OF SAMPLES FOR RADIOACTIVE ISOTOPE TRACER STUDIES

[75] Inventor: Niilo H. Kaartinen, Turku, Finland

[73] Assignee: Packard Instrument Company, Inc., Downers Grove, Ill.

[ * ] Notice: The portion of the term of this patent subsequent to Dec. 23, 1986, has been disclaimed.

[22] Filed: Aug. 2, 1972

[21] Appl. No.: 277,261

Related U.S. Application Data
[63] Continuation of Ser. No. 728,939, May 14, 1968, abandoned.

[52] U.S. Cl. ............................ 423/580; 423/437; 423/644; 423/658; 23/252 R; 260/583 R; 252/301.1 R; 252/301.1 W
[51] Int. Cl.² ..................... C01B 5/02; C01B 31/20; C09K 11/04
[58] Field of Search .......... 423/659, 580, 437, 648, 423/644; 252/301.1 R, 301.1 W; 23/230, 230 PC

[56] References Cited
UNITED STATES PATENTS

| | | | |
|---|---|---|---|
| 2,690,380 | 9/1954 | Taylor | 423/580 |
| 3,019,088 | 1/1962 | Vielstich et al. | 423/580 |
| 3,058,811 | 10/1962 | Shay | 423/580 |
| 3,305,318 | 2/1967 | Bennet | 23/230 |
| 3,355,252 | 11/1967 | De Blick | 23/230 X |
| 3,372,989 | 3/1968 | Macklin | 423/580 |
| 3,508,877 | 4/1970 | Heacock | 23/230 |
| 3,627,487 | 12/1971 | Jepson | 423/437 |
| 3,682,598 | 8/1972 | Kaartinen | 423/659 |

OTHER PUBLICATIONS
"Organic Scintillation Detectors" by E. Schram and R. Lambaert, 1963 Ed., pp. 76, 77, 80–83 and 85, Elsevier Pub. Co., New York.

Primary Examiner—Edward Stern
Attorney, Agent, or Firm—Leydig, Voit, Osann, Mayer & Holt, Ltd.

[57] ABSTRACT

Method and apparatus for the processing of fluid materials, particularly in the preparation of samples for radioactive isotope tracer studies by combustion of starting materials containing such isotope tracers. The sample is burned in a combustion chamber which tapers upwardly and inwardly above the sample receptacle so as to approximate the shape of the flame of a burning sample, and the combustion products are continuously exhausted from the combustion chamber and passed through a heat exchanger which condenses the condensable vapors in the combustion products. The condensed vapors are then separated from the gases, and the gases are passed into a reaction column if there is a radioactive isotope tracer remaining in gas form. Oxygen is fed into the combustion chamber at a controlled rate during combustion, and after combustion nitrogen gas is fed into the combustion chamber and exhausted therefrom through the heat exchanger and into the separating means, so as to purge the system of any remaining gaseous production products. A liquid scintillator, and a liquid solvent if desired, are passed through the heat exchanger into the separating means after each combustion so as to recover any residual condensed vapors. In the reaction column, the gas containing the radioactive isotope tracer is reacted with a trapping agent in a column comprising a series of smoothly contoured reaction chambers interconnected by smoothly contoured necked down portions. After all the gases have been passed through the column, the direction of gas flow is reversed in the column so as to discharge the reaction product into a counting vial. A liquid scintillator, and a liquid solvent if desired, are then passed through the reaction column following the same procedure as followed previously for the trapping agent, thereby recovering all the reaction product from the column.

17 Claims, 4 Drawing Figures

METHOD AND APPARATUS FOR PROCESSING FLUID MATERIALS PARTICULARLY IN THE PREPARATION OF SAMPLES FOR RADIOACTIVE ISOTOPE TRACER STUDIES

This application is a continuation of my copending application Ser. No. 728,939, filed May 14, 1968, and entitled "Method and Apparatus For Processing Fluid Materials, Particularly In the Preparation of Samples for Radioactive Isotope Tracer Studies", now abandoned.

CROSS REFERENCE TO RELATED APPLICATIONS

| Serial No. | Filing Date | Patent No. | Inventor |
|---|---|---|---|
| 729,047 | May 14, 1968 | 3,542,121 | Niilo Kaartinen |
| 728,553 | May 13, 1968 | 3,485,565 | Niilo Kaartinen |
| 820,269 | April 29, 1969 | 3,682,598 | Niilo Kaartinen |
| 058,635 | July 27, 1970 | 3,761,228 | Niilo Kaartinen |

DESCRIPTION OF THE INVENTION

The present invention relates generally to the processing of fluid materials. In its principal application, the invention relates to methods and apparatus for the preparation of samples for radioactive isotope tracer studies and, more particularly, to an improved method and apparatus for preparing such samples by combustion of the starting material containing the isotope tracer.

It is a primary object of the present invention to provide an improved method and apparatus for the preparation of samples for radioactive isotope tracer studies, which reduce the sample preparation time far below the preparation times required by the methods and apparatus previously known for the preparation of such samples, with corresponding increases in the sample preparation rate. In this connection, a related object of the invention is to provide such an improved method and apparatus which permit a technician to prepare a much greater number of samples in any given work period, thereby improving the efficiency and reducing the cost of such preparation procedures.

Another important object of the present invention is to provide an improved sample preparation method and apparatus of the foregoing type which significantly increase the efficiency of the isotope recovery from the starting material. More particularly, it is a specific object of this invention to provide such a method and apparatus which are capable of recovering essentially 100% of the isotope present in the starting material.

A further significant object of this invention is to provide an improved sample preparation method and apparatus of the type described above which virtually eliminate the memory of the apparatus so that the amount of isotope tracer in any given sample prepared thereby is substantially independent of any previous preparations carried out in the same apparatus. Thus, a related object of the invention is to provide such an improved method and apparatus which greatly improve the reliability of the resultant samples and the data derived therefrom.

Still another object of the invention is to provide such an improved sample preparation method and apparatus which are capable of providing radioactive samples containing little or no oxygen, thereby minimizing the quenching effects caused by oxygen in such samples during analysis thereof. Accordingly, a related object of the invention is to provide such an improved method and apparatus which facilitate analysis of the resulting samples.

A specific object of one particular aspect of the invention is to provide an improved combustion chamber for burning liquid or solid samples in an open system so that the combustion products are continuously removed from the combustion chamber, and including means for facilitating thorough cleaning of the chamber in a rapid and efficient manner after each combustion. Thus, a related object of this aspect of the invention is to provide such an improved combustion chamber which has virtually no memory, even when used to burn radioactive samples.

In another aspect of the invention, it is an object to provide an improved heat exchanger for condensable vapors which provides an extremely high heat transfer with only a small volume and surface area and in a very short time period. In this connection, it is also an object of this aspect of the invention to provide such an improved heat exchanger which is capable of receiving the products of combustion of a radioactive sample and continuously condensing the vapors therefrom in a rapid and efficient manner.

Yet another object of a further particular aspect of the invention is to provide an improved gas-liquid reaction column which achieves a high reaction rate between the gas and liquid, and yet can be thoroughly cleaned in a matter of seconds between successive batch-type reactions so that the column has virtually no memory, even when used to react radioactive materials.

Another important object of the present invention is to provide an improved radioactive sample preparation apparatus which achieves all the objectives mentioned above at a low cost and with the use of highly reliable components, and which is easy to operate.

Other objects and advantages of the invention will become apparent from the following detailed description and upon reference to the accompanying drawings, in which.

Figure 1:
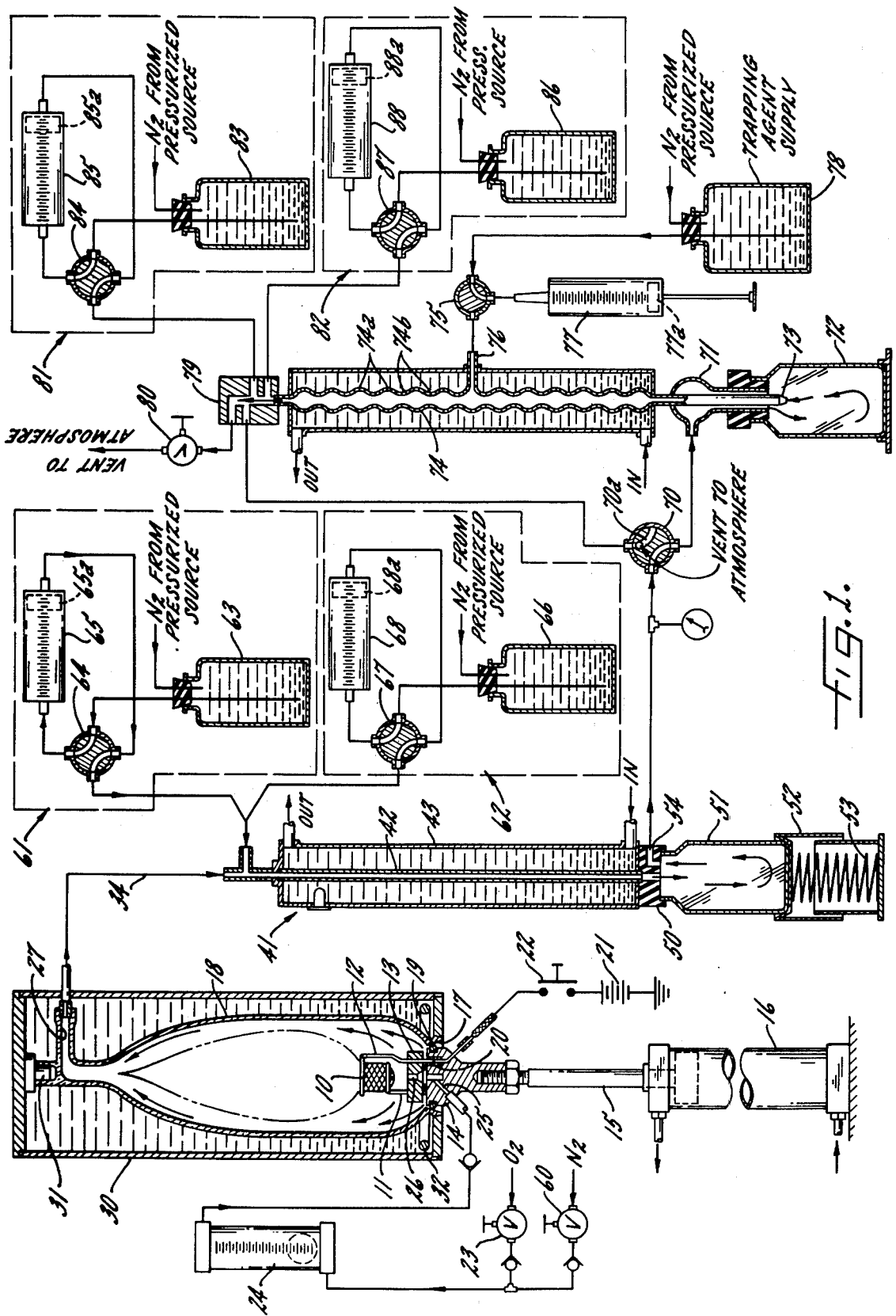
FIG. 1 is a schematic diagram of a sample preparation system embodying the present invention, for use in the preparation of samples for radioactive isotope tracer studies.
Figure 2:
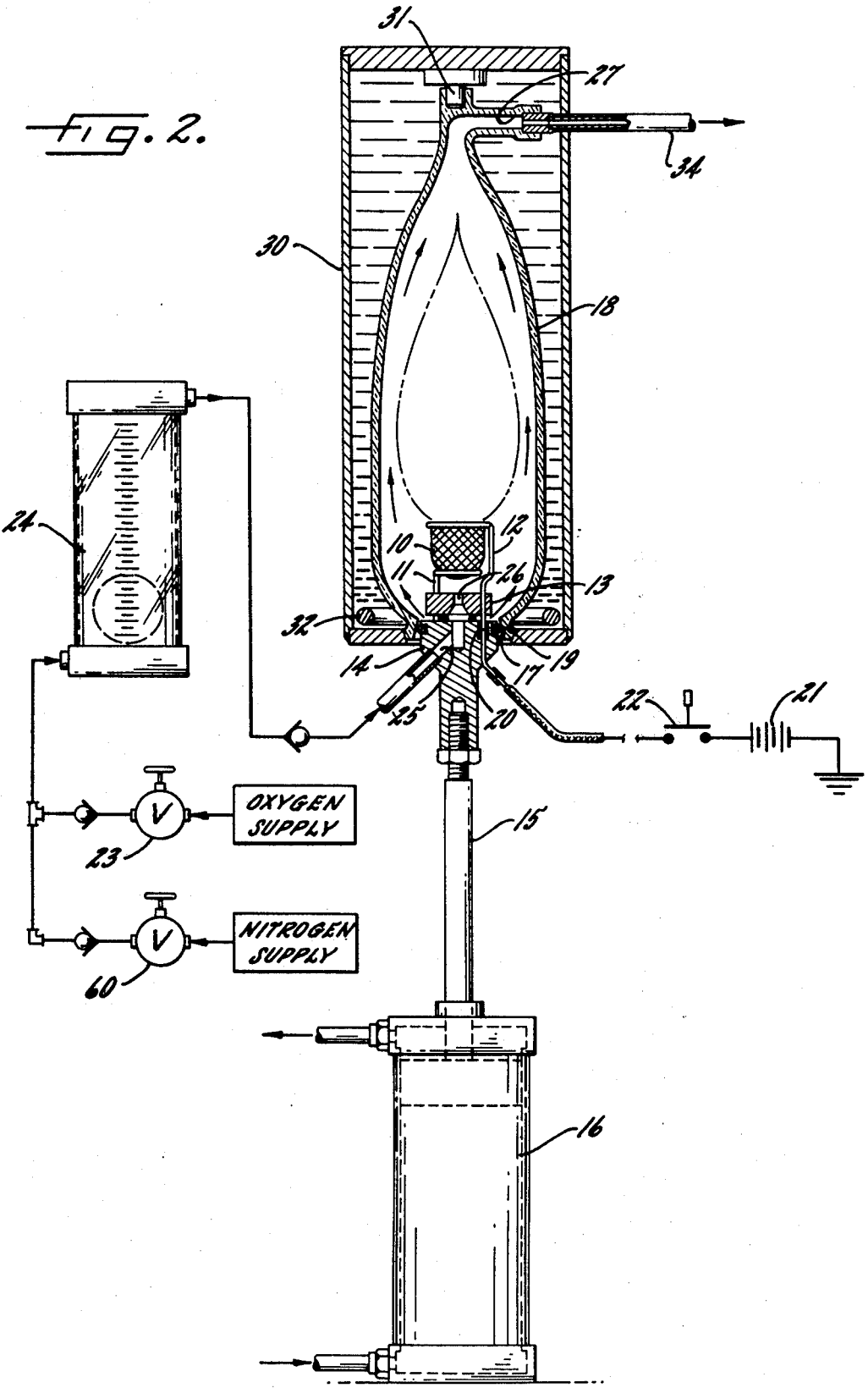
FIG. 2 is an elevation view, partially in section, of combustion apparatus for use in the preparation of samples for radioactive isotope tracer studies, and including a schematic diagram of a portion of the fluid and electrical systems associated therewith.
Figure 3:
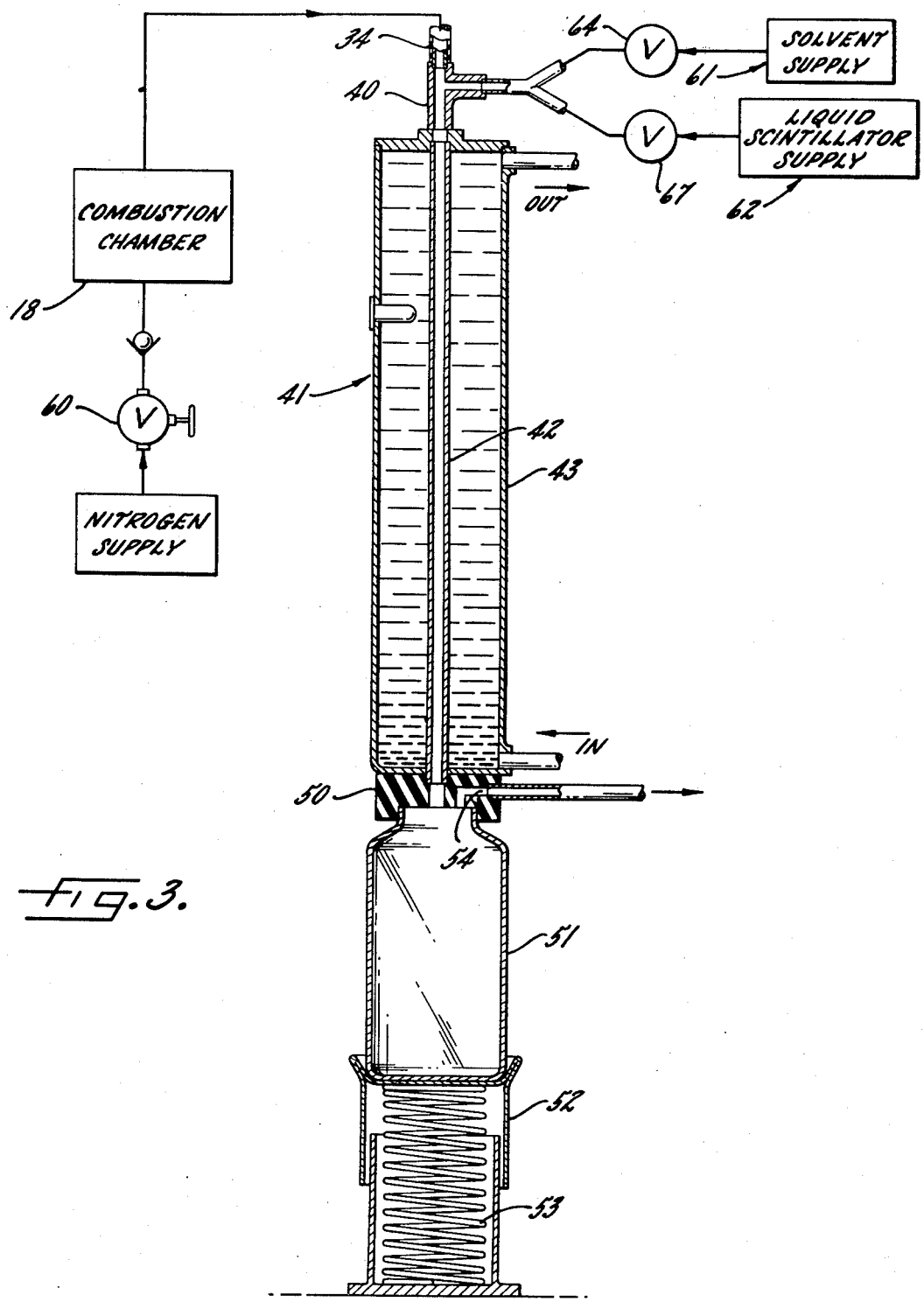
Figure 4:
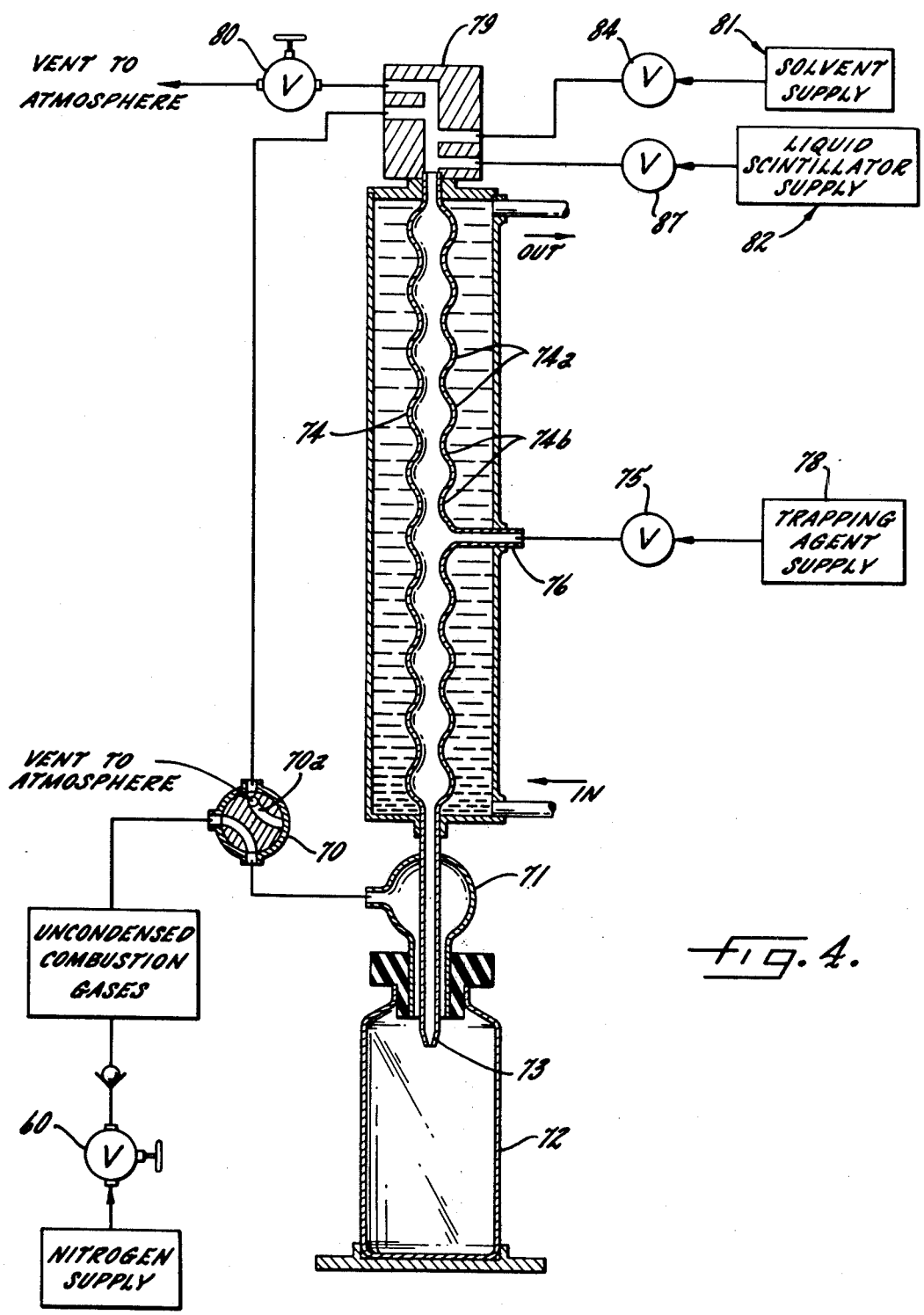

FIG. 3 is a sectional elevation view of a heat exchanger and condensate separation means for use in the sample preparation system of FIG. 1, and including a schematic diagram of a portion of the fluid system associated therewith; and FIG. 4 is a sectional elevation view of a reaction column for use in the sample preparation system of FIG. 1 and including a schematic diagram of a portion of the fluid system associated therewith.

While the invention will be described in connection with certain preferred embodiments, it will be understood that it is not intended to limit the invention to these particular embodiments. On the contrary, it is intended to cover all alternatives, modifications and equivalent arrangements as may be included within the spirit and scope of the invention as defined by the appended claims.

Turning now to the drawings, in FIG. 1 there is illustrated a sample preparation system for use in the preparation of samples for radioactive isotope tracer studies, such as studies involving tissue distribution and residue levels of drugs in plants and animals. In the preparation of such samples, a sample of the starting material containing the radioactive isotope tracer, such as a sample of the plant or animal tissue, is burned to convert the carbon in the starting material to carbon dioxide and the hydrogen to water, and the radioactive isotope tracer is then recovered from the resulting combustion products. For example, if the particular radioactive isotope tracer employed is $^{14}C$, it appears in the combustion products as $^{14}CO_2$ gas; if the tracer is tritium ($^3H$), it appears in the combustion products as $^3H_2O$ in the form of a condensable vapor.

In order to provide samples which can be analyzed for radioactivity, the compounds containing the isotope tracers are recovered from the combustion products, and separated from any materials therein which might interfere with the radioactivity determination. For example, the $^3H_2O$ is recovered by cooling the combustion products to condense the vapors therein, including the $^3H_2O$, after which the condensed vapors are separated from the remaining gases. The $^{14}CO_2$ may also be recovered by condensation or freezing at extremely low temperatures, such as by the use of liquid nitrogen for example, but it is more conventional to react the $^{14}CO_2$ with a liquid trapping agent such as ethanolamine; the resulting reaction product is then recovered and mixed with a liquid scintillator to provide a sample suitable for use in making a radioactivity determination.

Referring now more specifically to FIG. 1, the sample to be burned is placed in a sample basket 10 which forms a part of the electrical ignition system, and also functions as a catalyst for efficient combustion for the sample contained therein. The basket 10 is suitably made of platinum or a platinum-rhodium alloy, so that the basket can be used both as an electrical resistor in the ignition system and as a catalyst for the combustion of the sample. A pair of electrical conductors 11 and 12 extend upwardly from a mounting plate 13, to support the basket 10 at the upper and lower ends thereof, while also making electrical contact with the basket to connect it into the electrical ignition system. The conductors 11 and 12 extend vertically down through the plate 13 and terminate in depending connector pins beneath the plate 13.

In order to facilitate the loading of successive samples, the mounting plate 13 is supported on the top of a small platform 14 threaded on to the end of a pneumatic piston rod 15. To load a sample in the basket 10, the pneumatic cylinder and piston assembly 16 associated with the rod 15 is actuated to retract the piston rod 15, thereby lowering the basket 10 through an opening 17 in the bottom of a combustion chamber 18. The sample is then loaded in the basket, and the cylinder and piston assembly 16 is actuated to advance the rod 15 and thereby raise the basket 10 through the opening 17 into the combustion chamber 18. As the platform 14 enters the opening 17, a sealing ring 19 mounted in a groove in the outer periphery of the platform 14 engages the tapered walls of the opening 17 to form a gas-tight seal therewith.

For the purpose of igniting a sample contained in the basket 10 after it has been raised into the combustion chamber 18, the connector pins depending from the plate 13 fit into complementary electrical receptacles 20 in the top of the platform 14. The receptacles 20, in turn, are connected to an electrical igniter circuit including a power source such as battery 21 and an ignition switch 22 for applying an electrical voltage across the basket 10, which serves as a resistive type heating element in the igniter system. Thus, the sample is ignited by simply closing the switch 22, which is opened again as soon as combustion has been initiated.

In order to supply the oxygen required for combustion of the sample contained in the basket 10, pure oxygen is supplied to the combustion chamber 18 through a valve 23, a flow meter 24, and a pair of cooperating passageways 25 and 26 formed in the platform 14 and the plate 13. The gas discharge passageway 26 in the plate 13 is positioned directly beneath the center of the basket 10, so that the oxygen is fed directly into the combustion zone. The oxygen flow rate is adjusted, via the valve 23 and the flow meter 24, to a level slightly above that required to support combustion of the sample in the basket 10, so that there is a slight excess of oxygen within the combustion chamber. Consequently, there is generally a relatively thin layer of an oxygen-rich atmosphere between the combustion chamber 18, as indicated by the arrows in the drawing. This excess oxygen rises through the combustion chamber and is exhausted from the combustion chamber 18 along with the combustion products through a lateral exit 27 at the top of the chamber.

In accordance with one aspect of the present invention, the combustion chamber is open at the upper end thereof with the sidewalls extending upwardly and inwardly above the sample basket so as to approximate the shape of the flame of a burning sample, thereby minimizing the volume of oxygen-rich atmosphere around the flame, and the walls of the combustion chamber are preheated so as to maintain the wall temperature above the condensation temperature of the vapors contained in the combustion products. With this design, the combustion products tend to be swept directly into the exit 27, with the rising layer of oxygen-rich atmosphere along the chamber sidewalls tending to isolate the combustion products from the sidewalls. Moreover, any combustion products that do contact the chamber walls remain in the gas state, even during initiation of the combustion, because the walls are pre-heated and maintained at a temperature above the condensation temperature. Thus, in the illustrative embodiment of the combustion chamber the walls of the combustion chamber 18 extend vertically upwardly past the sample basket 10, and then slope inwardly above the basket so as to approximate the shape of the flame represented in broken lines. Surrounding the combustion chamber 18 is a cylindrical vessel 30 which defines an annular cavity around the outer surface of the chamber 18 for receiving a preheating fluid. To center the combustion chamber 18 within the vessel 30, the upper end thereof meshes with a complementary mounting element 31, while the lower end fits into a complementary hole in the bottom wall of the vessel 30.

Prior to ignition of the sample contained in the basket 10, the fluid contained in the annular cavity between the combustion chamber 18 and the vessel 30 is heated by means of a heating coil 32 at the lower end of the cavity. The fluid distributes this heat along the walls of the combustion chamber 18 so that the walls are uniformly heated to a temperature above the condensation temperature of the vapors contained in the combustion products to be produced. It has been found that the preheating of the combustion chamber walls to maintain the combustion products in gaseous form even during ignition, combined with the flame-shaped configuration of the chamber, permits the combustion products to be exhausted from the combustion chamber, on a continuous basis, so efficiently that there is virtually no residue of combustion products deposited on the chamber walls. The illustrative system also prevents condensation within the exit 27 of the combustion chamber 18, since the exit is also surrounded by the preheated fluid in the annular cavity between the combustion chamber 18 and the surrounding vessel 31.

As the exhausted gases leave the exit 27, they enter a transfer tube 34 which is insulated to maintain the fluids passing therethrough in a gaseous state. In the particular embodiment illustrated, the transfer tube 34 is double walled with a metallic inner shell and an insulating outer shell to minimize the heat loss therethrough. From the transfer tube 34, the gaseous combustion products are passed through a T connection 40 into a heat exchanger 41 for cooling the exhausted combustion products to condense the vapors therein. The heat exchanger 41 includes an inner member 42 forming a fluid passageway for receiving the combustion products from the tube 34, and an outer shell 43 defining an annular cavity around the inner member 42 for receiving a cooling liquid to maintain the walls of the inner passageway at a temperature at least as low as the condensation temperature of the vapors passing therethrough. When the radioactive isotope tracer is in the form of a condensable vapor, such as $^3H_2O$ for example, the heat exchanger 41 functions to convert the tracer from a vapor to liquid form. In cases where the radioactive isotope tracer is in the form of a gas to be reacted with a trapping agent, for example, the heat exchanger 41 functions to remove the condensable vapors from the tracer gas before it is reacted with the trapping agent.

In accordance with another significant aspect of this invention, the fluid passageway of the heat exchanger is, formed of thermally conductive material designed to provide laminar flow of gases and vapors passing therethrough in the absence of condensation, and the cross section of the fluid passageway is sufficiently small in at least one direction transverse to the fluid flow to provide capillary attraction on the type of liquid condensed within the passageway. Thus, in one preferred embodiment of the invention, the inner member 42 comprises a straight thin walled metal tube having an inside diameter of about 0.05 inch, with a wall thickness of about 0.004 inch, and a length of about 5 inches. Although both the volume and the heat transfer surface area of such a tube are obviously very small, it has been found that such a heat exchanger is capable of reducing the temperature of the combustion gases to the condensation temperature with such a high degree of efficiency that virtually 100% of the condensable vapors can be recovered in liquid form at the outlet end of the heat exchanger. Moreover, this heat transfer is effected without producing a high backpressure or otherwise inhibiting the exhaustion of the combustion products from the combustion chamber directly upstream of the heat exchanger inlet.

Although it is not intended to limit this aspect of the invention to any particular theory, it is believed that the fluid passageway designed in accordance with this invention causes droplets of liquid condensate to form along the walls of the passageway, thereby providing extremely efficient heat transfer conditions. This dropwise condensation may be caused or promoted by the capillary nature of the fluid passageway. When the fluid passageway in the heat exchanger is in tubular form as in the illustrative embodiment, a pulsating pressure is detected at the inlet of the passageway, and it is believed that drop-wise condensation may account for this pulsating pressure. It will be appreciated, however, that the fluid passageway may have forms other than tubular, such as a narrow slot, since capillary attraction is present whenever the surface of a liquid where it is in contact with a solid is elevated by the relative attraction of the molecules of the liquid for each other and for those of the solid.

As another feature of the present invention, a separating means is connected to the outlet end of the heat exchanger for receiving the combustion products, including the condensed vapors, from the heat exchanger and separating the condensed vapors from the remaining gas products, and control means are associated with the combustion chamber for terminating the oxygen supply and supplying an inert gas to the combustion chamber upon completion of the burning of each sample so as to sweep any residual combustion products out of the chamber and on through the heat exchanger into the separating means. Thus, in the illustrative system, a resilient connector 50 is provided at the lower end of the heat exchanger 41 for connecting the outlet of the fluid passageway member 42 to a conventional sample or counting vial 51. The vial 51 is supported on a platform 52 which is biased upwardly against the connector 50 by means of a biasing spring 53 to provide a gas-tight seal around the upper periphery of the vial. As the combustion products are discharged from the lower end of the heat exchanger 41, they flow downwardly into the sample vial 51 so that the liquids are retained in the vial by gravity, while the gases continue on through a discharge passageway 54 formed in the resilient connector 50.

When the combustion of a given sample has been completed, the valve 23 is closed to terminate the oxygen supply to the combustion chamber, and a valve 60 is opened to supply an inert gas such as nitrogen to the combustion chamber via the same flow meter 24 and passageways 25, 26 previously used to supply the oxygen. This inert gas, which is supplied under a slight pressure, sweeps upwardly through the combustion chamber 18 so as to purge the chamber of any remaining combustion products, and continues on through the chamber exit 27, the transfer tube 34, and the heat exchanger 41. Consequently, it can be seen that the entire system from the combustion chamber 18 to the sample vial 51 is immediately purged of all gaseous combustion products following each sample combustion, and the purging gas also tends to sweep any remaining liquid condensate out of the heat exchanger. Moreover, since the inert purging gas is discharged from the heat exchanger 41 into the headspace of the sample vial 51 which is used as a part of the liquid-gas separating means, it may also be used to purge oxygen from the vial headspace to avoid the quenching effect of such oxygen during analysis of the resultant sample for radioactivity. Thus, when the sample vial 51 is disconnected from the resilient connector 50 to place a sealing cap on the vial, the throat of the vial may be maintained directly under the nitrogen discharge from the connector 50 by simply tilting the vial laterally, so that the nitrogen purges the headspace of the vial by displacing any oxygen remaining therein to the atmosphere. As will be apparent to those familiar with this art, this is an important feature because oxygen is a severe quenching agent, i.e., it distorts the radioactivity measurements made by liquid scintillation counting techniques unless certain steps are taken to compensate for the effect of the quenching agent. Although several means of compensating for such quenching effects are known, they complicate the radioactivity measuring procedure.

After the purging of the combustion chamber and the heat exchanger, the inert purging gas is preferably turned off by closing the valve 60, and the inlet of the heat exchanger 41 may be sequentially connected to a pair of liquid supply systems generally indicated at 61 and 62. The first supply system 61 includes a supply vessel 63 containing a liquid solvent of the type conventionally used in the preparation of samples to be subjected to sub-freezing temperatures, so as to maintain the sample in a liquid state. It will be understood that this first liquid supply system 61 is not normally used in the preparation of samples to be handled at above-freezing temperature. Referring now more specifically to the liquid supply system 61, an inert gas such as nitrogen is supplied to the headspace of the supply vessel 63 under a slight pressure, so as to force the liquid solvent through a valve 64 into a metering dispenser 65 including a movable piston 65a. As long as the valve 64 remains in the position illustrated in FIG. 1, the piston 65a in the metering dispenser 65 remains in the position illustrated in FIG. 1 and no liquid flows out of the dispenser because the output thereof is effectively closed. However, when the valve 64 is turned 90° to its second position, the pressure of the fluid from the supply vessel 63 urges the piston 65a to the left as viewed in FIG. 1 until it reaches a preselected stop position, thereby metering a preselected quantity of liquid through the valve 64 and the T connection 40 into the heat exchanger 41. As the piston 65a moves to the left, the supply of liquid within the dispenser 65 is continuously replenished through the right hand end thereof. Thus, when the metered quantity of liquid solvent has been dispensed, the system is ready to dispense the same preselected quantity of liquid the next time the valve 64 is turned 90°. It will be understood that the piston 65a moves alternately to the left and to the right during successive dispensing operations.

The second liquid supply system 62 is used to feed a preselected quantity of liquid scintillator into the heat exchanger 41 in the same manner described above for the solvent supply system 61. Thus, the liquid scintillator is fed from a supply vessel 66 through a four-way valve 67 into a metering dispenser 68, and is dispensed alternately from opposite ends of the dispenser in response to successive 90° turns of the valve 67. From the valve 67, the liquid flows into the T connection 40 and then downwardly through the heat exchanger 41 into the vial 51.

In order to insure that all the liquid supplied to the T connection 40 from the liquid supply systems 61, 62 flows downwardly through the heat exchanger 41, a restriction (not shown) may be formed in the transfer line 34 to prevent liquid from backing up into the line 34 from the T connection 40. As the liquids from the systems 61, 62 flow downwardly through the heat exchanger 41, they are discharged through the connector 50 into the sample vial 51, where they are retained along with the condensed vapors collected previously.

It will be appreciated that the connection of the two liquid supply systems to the heat exchanger inlet not only provides a convenient means of supplying these liquids to the sample vial connected to the outlet of the heat exchanger, but also insures that substantially all the condensed vapors are recovered from the walls of the heat exchanger tube 42. In this connection, one of the important advantages of the illustrative system is that the radioactive tracer never passes through any valves or other devices having movable parts, thereby facilitating recovery of the tracer and elimination of equipment memory. Moreover, due to the small volume of the heat exchanger, any fluid contained therein changes at a relatively high rate when fluid is flowing therethrough. To insure that all the liquids fed into the heat exchanger 41 are discharged therefrom, it is preferred to resume the nitrogen flow through the heat exchanger, via the combustion chamber, for a short interval of about five seconds, for example, after the liquid flow from the two systems 61, 62 has been terminated. (This nitrogen flow can also be used to purge the headspace of the vial 51 as it is removed from the connector 50, prior to placement of the cap thereon, in the manner described previously.) With this system, it has been found that essentially 100% of the radioactive isotope tracer present in the starting material can be recovered in the sample vial 51, when the isotope is in the form of a condensable vapor.

In accordance with a further important aspect of this invention for recovering tracers by reaction with a trapping agent, the gases which are separated from the condensed vapors are passed into a reaction column including means for receiving a liquid trapping agent and reacting the gases with the trapping agent as the gases flow through the column. The reaction column is also provided with means for reversing the direction of the gas flow through the column for discharging the trapping agent and the reaction product from the column, and a sample vial is connected to the reaction column for receiving the trapping agent and reaction product from the column in response to the reversal of the gas flow. Thus, in the illustrative system, the gases discharged from the first sample vial 51 through the discharge passageway 54 in the resilient connector 50 are passed through a valve 70 which, when in the position shown in FIG. 1, conducts the gases through a connector 71 into a second sample vial 72. From the sample vial 72, the gases enter the lower end of a depending stem 73 of a reaction column 74 comprising a series of smoothly contoured reaction chambers 74a interconnected by smoothly contoured necked down portions 74b with the interconnecting walls of the chambers 74a and the necked down portions 74b forming a smooth curvilinear configuration. When the reaction column 74 is used, i.e., when a radioactive isotope tracer is to be recovered by reaction with a trapping agent, a valve 75 is turned 90° from the position shown in FIG. 1 so as to feed a preselected amount of liquid trapping agent into an inlet stem in the middle of the reaction column 74 just after the oxygen supply to the combustion chamber 18 is turned on. Thus, gas is already flowing upwardly through the reaction column 74 when the liquid trapping agent first enters the column. With the particular configuration of reaction column provided by this invention, it has been found that the liquid trapping agent becomes uniformly distributed throughout the various reaction chambers 74a, and such distribution is maintained, as long as gas flows continuously up through the column 74. That is, the upward gas flow through the reaction column causes the liquid trapping agent to become distributed along the walls of the bulbous or enlarged reaction chambers 74a while preventing the trapping agent from flowing down through the elongated depending stem 73 at the bottom of the reaction column, so that no liquid trapping agent enters the vial 72.

In order to feed a preselected amount of trapping agent to the reaction column, the liquid is supplied by means of a metering device 77 having a movable piston therein with a predetermined stop position. Thus, the piston 77a is stopped at the same position during each feeding operation, so that the same amount of liquid trapping agent will be supplied for each sample. As long as the valve 75 is in the position illustrated in FIG. 1, the piston 77a in the metering device 77 remains in the position shown in FIG. 1 and no liquid flows into the inlet stem 76. When the valve is turned 90° clockwise, the output of the device 77 is connected to the inlet stem 76, and subsequent advancement of the plunger 77a dispenses a preselected quantity of trapping agent into the reaction column 74; although a manually actuated plunger 77a is shown in the drawings, it will be understood that the dispensing of the liquid trapping agent could be made automatically responsive to the turning of the valve 75. After the metered amount of trapping agent has been fed into the reaction column, the valve 75 is returned to its normal position as illustrated in FIG. 1, and the metering device 77 is automatically refilled with liquid trapping agent from a supply bottle 78, the liquid being fed from the bottle 78 into the metering device 77 by means of pressurized nitrogen in the headspace of the supply bottle 78.

As the gases containing the radioactive isotope tracer, such as $^{14}CO_2$ for example, are passed upwardly through the reaction column, the radioactive compound is reacted with the trapping agent, such as ethanolamine for example, to form a reaction product which is held within the reaction chambers 74a along with the liquid trapping agent. The amount of reaction product contained in the series of reaction chambers 74a varies along the length of the reaction column, but it has been found that the reaction effected by the particular reaction column configuration provided by this invention traps over 99% of the isotope tracer. The unreacted gases are exhausted from the upper end of the reaction column through a connector member 79 and vented to the atmosphere through a valve 80.

To control the reaction temperature within the column 74, a heat transfer fluid is passed through an annular jacket surrounding the column 74. In this connection, it has been found that the reaction column provided by this invention provides effective heat transfer with a high degree of efficiency when used to carry out gas-liquid reactions. It is believed that the interaction of the upwardly flowing gas with the liquid that is held within the enlarged reaction chambers 74a brings all portions of the liquid into intimate contact with the column walls, thereby effecting efficient heat transfer between the liquid and the column walls.

After the sample combustion has been completed, the flow of nitrogen gas is continued for a suitable purging period, e.g. 30 seconds, and the valve 70 is then turned 90° so as to conduct the purging nitrogen gas into the upper end of the reaction column 74, thereby effecting a reversal of the direction of gas flow through the column. As the gas flows downwardly through the reaction column 74, it sweeps the liquids contained therein, including the reaction product formed by reaction of the liquid trapping agent with the gas compound containing the isotope tracer, into the sample vial 72. The gases are discharged from the vial 72 upwardly through the connector 71 and vented to the atmosphere through the valve 70 via passageway 70a therein.

The valve 70 is then returned to its original position to resume the gas flow upwardly through the reaction column, and the connector 79 at the upper end of the reaction column 74 may be sequentially connected to a pair of liquid supply systems generally indicated at 81 and 82. The first supply system 81 includes a supply vessel 83 containing a liquid solvent to be used to dissolve the reaction product formed by reaction of the isotope compound with the trapping agent; the solvent may also serve to maintain the resultant sample in a liquid condition where it is to be handled at sub-freezing temperatures, as described previously in connection with the liquid supply system 61. An inert gas such as nitrogen is supplied to the headspace of the supply vessel 83 under a slight pressure so as to force the liquid solvent through a valve 84 into a metering dispenser 85 including a movable piston 85a. As described previously in connection with the liquid dispensers 65 and 68, the piston 85a moves back and forth within the dispenser 85 in response to successive 90° turns of the valve 84, so as to feed a preselected quantity of liquid solvent through the valve 84 into the connector 79 each time the valve 84 is turned 90°. This liquid flows downwardly into the reaction column 74 and is distributed therethrough in the same manner described previously for the liquid trapping agent supplied through the inlet stem 76. It has been found that the combination of the upward gas flow and the liquid input at the top of the column, provides a scrubbing action on the inside walls of the reaction column so that substantially all the reaction produce contained therein is recovered in the sample vial 72. In fact, it has been found that the recovery effected by this reaction column is so effective that it has substantially no memory whatever, and over 99% of the isotope tracer is recovered in the vial 72.

After the first liquid has been dispensed into the top of the reaction column, the nitrogen flow is continued upwardly through the column for a period of about 15 to 45 seconds, depending upon the concentration of $CO_2$ relative to the trapping agent. The valve 70 is then again turned 90° to reverse the gas flow through the reaction column, thereby sweeping the liquid solvent downwardly through the reaction column into the sample vial 72. The valve 70 is then again returned to its original position so that the inert purging gas once again flows upwardly through the reaction column, and the liquid scintillator is metered into the upper end of the reaction column from the second liquid supply system 82. More particularly, liquid scintillator is fed from a supply bottle 86 through a four-way valve 87 into a metering dispenser 88. When the valve 87 is turned 90° from the position illustrated in FIG. 1, with the dispenser piston 88a in the position shown, a preselected quantity of liquid scintillator is forced out of the dispenser by the pressure of the nitrogen in the headspace of the bottle 86, thereby advancing the piston 38a to the left to force liquid through the valve 87 into the connector 79 at the top of the reaction column 74. Due to the upward gas flow through the reaction column, this liquid again provides a scrubbing action on the walls of the reaction column 74. After the liquid has been dispersed into the column, the upward nitrogen flow is continued for about 5 to 10 seconds, at which time the gas flow is again reversed in the column 74, by turning the valve 70, to discharge the liquid scintillator into the valve 72. In addition to providing a convenient means of admitting the liquid scintillator into the vial 72, the liquid supply systems associated with the reaction column 74 provide a rapid and efficient means of achieving recoveries in excess of 99% with attendant low memories of 1/1000 or less. Moreover, it will be appreciated that the isotope tracer is passed through only a single valve 70, and then only while it is in the gas form, thereby further facilitating complete recovery of the radioactive tracer.

In one example of the invention, ten one-gram samples of tritium-labelled samples were combusted in sequence in the same equipment, with a blank sample, i.e., a sample containing no radioactive tracer, being combusted after each labelled sample. The combustion of each sample was initiated by the electrical igniter, heated to a temperature of about 1500°C., and the oxygen flow rate was set at about two liters per minute. The pressure inside the combustion chamber during combustion was less than 0.1 atmosphere above atmospheric pressure. The walls of the combustion chamber were pre-heated and thermostatically maintained at approximately 170°C. which was sufficient to prevent any noticeable condensation of the combustion products on the inside walls of the combustion chamber. During combustion, the combustion products were continuously exhausted through the upper end of the combustion chamber into a heat exchanger, comprising a straight tube of stainless steel having an inside diameter of 0.080 inch, a wall thickness of 0.020 inch, and a length of 10.00 inches. The walls of the tube were maintained at a temperature of about 0°C. From the heat exchanger, condensed vapors including condensed $^3H_2O$ dripped into the counting vial connected to the lower end of the heat exchanger, while the remaining gases passed on through the vial and were vented to the atmosphere.

The combustion of each sample was completed in about 45 seconds, after which the oxygen was turned off and the nitrogen supply to the combustion chamber was turned on so that nitrogen was fed into the combustion chamber at a rate of seven liters per minute for about five to ten seconds. The nitrogen was then shut off and a selected quantity of dioxane (liquid scintillator) was fed from the metering dispenser into the inlet of the heat exchanger. The metering dispenser was preset to feed ten milliliters of the liquid scintillator into the heat exchanger over a period of about five seconds, after which the liquid supply line to the inlet of the heat exchanger was closed, and the nitrogen feed to the combustion vessel was resumed for an additional five seconds at a rate of about four liters per minute. During this final nitrogen feed, the counting vial was removed from the resilient connector at the outlet of the heat exchanger and tilted with the open mouth of the vial positioned below the passageway from the heat exchanger outlet so that the nitrogen supplied to the counting vial during this interval purged the vial of oxygen. The vial cap was then quickly threaded onto the vial to seal the sample contained therein in a nitrogen atmosphere, and the sample was analyzed for radioactivity.

The radioactivity level of the tracer in the starting material placed in the combustion chamber was 100,000 disintegrations per minute (dpm). When the sample collected in the counting vial was analyzed for radioactivity, a count of 42,000 counts per mintute (cpm) was measured. The counting efficiency of the analytical method was determined to be 42% so that the measured count of 42,000 cpm indicated that there was no loss whatever, i.e., there was 100% recovery of the radioactive material. To check the accuracy of the radioactivity measurement made for the recovered material, the same amount and type of radioactive isotope tracer that was injected into the original starting material was placed in a second counting vial and analyzed for radioactivity in the same equipment used to analyze the recovered sample. The count measured for this second counting vial was identical to the measurement for the first sample, i.e., the count was 42,000 cpm in each case, thereby confirming that the recovery was in fact 100%. Over the series of ten samples, the standard deviation of recovery was determined to be 0.7%, which is about the same degree of variability accounted for by statistical variations in the samples plus the accuracy of the analytical instrument without automatic standardization. Based on a comparison of the counts of the radioactive samples and the alternate blank samples, a memory of 1/10,000 or less was obtained consistently throughout the entire series of samples. The 42% counting efficiency compares wih maximum efficiencies of 25 to 36% obtainable by comparable methods used previously, the improvement being due in large measure to the fact that there was little or no oxygen present in the sample so that quenching effects were minimized or perhaps even eliminated. In addition to the increase in efficiency, there was a corresponding reduction in background, so that the resulting figure of merit (efficiency squared divided by background) was significantly increased. For example, with the 42% efficiency, the background was 27 so that the figure of merit was 650, which compares with a figure of merit of 370 obtainable by the conventional previous methods. The total time required to prepare the above samples was such that about 30 to 40 samples could be prepared per hour.

In another example of the invention, 300 milligrams of double-labelled ($^3H$ and $^{14}C$) material was placed in the combustion chamber and burned in the same manner described above in the previous example. The only differences in the combustion step of this example were that the oxygen flow rate was initially set at about 0.1 liter per minute, and immediately after the oxygen was turned on 2.7 milliliters of ethanolamine (trapping agent) were manually injected into the reaction column. After the ethanolamine was injected into the reaction column, the oxygen feed rate was gradually increased to one liter per minute, and at the same time the pressure in the gas feed line to the reaction column was increased by turning the valve in the atmosphere vent line toward the closed position until the pressure reached 0.3 atmosphere above atmospheric pressure.

At this point, the sample was ignited in the combustion chamber in the same manner described in the example above. A white flame was initially produced due to the burning of hydrogen (which burns more rapidly than the carbon and produces a white flame). As this white flame began to diminish, the oxygen flow rate was gradually decreased to about 0.3 liters per minute to complete the combustion of the carbon. The exhaust gases from the combustion chamber were initially rich in water due to the combustion of the hydrogen, and subsequently become richer in carbon dioxide due to the combustion of the carbon. The water was condensed and collected in the first counting vial, while the $CO_2$ gas was passed on to the reaction column containing ethanolamine as a trapping agent; as the $CO_2$ passed upwardly through the reaction column, it reacted with the ethanolamine to form a carbamate reaction product. After the combustion was completed, the oxygen was turned off and the nitrogen turned on at a flow rate of 0.3 liters per minute and maintained for about 15 seconds to purge the system of gaseous combustion products. With the nitrogen flow continuing, the valve connected between the first vial and the reaction column was turned to its second position so that the nitrogen flow was fed into the top of the reaction column rather than the bottom, thereby reversing the nitrogen flow through the column to sweep the liquid reaction product, as well as any unreacted trapping agent, downwardly through the reaction column and into the second counting vial. The excess gases were discharged through the connector 71 and the valve 70. After the reaction product was collected in the second counting vial, the valve 70 was returned to its original position, with the nitrogen flow rate being maintained at about 0.3 liter per minute. The nitrogen was then turned off, and the liquid scintillator was fed into the inlet of the heat exchanger in the same manner described above. The nitrogen feed was then turned on again to purge the headspace of the first counting vial in the same manner described above, after which the vial was then removed and replaced with a new vial which simply served as a conduit for the nitrogen gas to be flowed through the system for the balance of the preparation procedure. At this point, the four-way valve associated with the metering device for the liquid solvent was turned to connect the output of the metering device to the top of the reaction column so that the pressure in the headspace of the solvent supply bottle forced a preselected quantity of liquid solvent into the reaction column. As this liquid passed downwardly through the column, the upwardly passing nitrogen gas coacted with the downwardly flowing liquid to create a turbulent condition within the reaction column. The nitrogen flow was maintained for 15 seconds and then again switched to the top of the reaction column so as to sweep the liquid downwardly through the column and into the counting vial. At this point, the valve 70 was returned to its original position so that the nitrogen flow once again entered the bottom of the column and flowed upwardly therethrough. At the same time, the four-way valve associated with the liquid scintillator supply system was turned to connect the output of the metering device to the top of the reaction column so as to feed a preselected metered amount of liquid scintillator into the top of the reaction column in the same manner described previously for the liquid solvent, except that the nitrogen flow was maintained for only 5 seconds, after which the valve 70 was again switched to its second position to conduct the nitrogen into the top of the column and sweep the liquid down into the counting vial. The nitrogen flow rate was then increased to a level of four liters per minute, and the second counting vial was removed from its stopper and tilted thereunder to purge the vial headspace in the same manner described previously for the first counting vial. At this point, the nitrogen flow was shut off and the sample preparation procedure was complete. The amount of liquid solvent fed into the reaction vessel was eight milliliters, and the amount of liquid scintillator was the same. The total sample preparation time for this double-labelled sample was such that 10 to 15 samples could be prepared per hour. The counting efficiency was 70%, the recovery was in excess of 99%, the standard deviation of recovery was 0.9%, and the memory was a maximum of 1/1000. The background was 37, so that the figure of merit was 133.

It will be understood from the foregoing description that the illustrative sample preparation system may be used to prepare samples from starting materials labelled with only a single tracer to be recovered either as a condensed vapor or by reaction with a trapping agent, or from double-labelled samples containing tracers to be recovered by both means. In the event that the material is labelled with only a single tracer to be recovered as a condensed vapor, the gases discharged from the first sample vial 51 are, of course, simply passed on through the balance of the system and vented to the atmosphere. In the case of a sample labelled with only a single tracer to be recovered by reaction with a trapping agent, it is not necessary to supply a liquid scintillator to the heat exchanger 41, although it may be desired to feed some other liquid through the heat exchanger in order to remove the condensed vapors therefrom between successive combustions. Similarly, there is no need to feed any liquids whatever into the reaction column 74 when the sample is labelled with only a single tracer to be recovered as a condensed vapor, since the gas is discharged from the vial 51 will normally be vented to the atmosphere via valve 70 during the preparation of such samples. If it is desired to prepare only tritium-labelled samples, for example, that portion of the system downstream of the vial 51 may even be eliminated.

It will also be appreciated that any of the manual operations required in the illustrative system may be readily converted to automatic operation. For example, the opening and closing of the oxygen and nitrogen valves 23 and 60, respectively, may be controlled by timing mechanisms according to a predetermined time schedule for particular types of samples. Similarly, the valves 64, 67, 75, 84, and 87 associated with the various liquid supply systems, as well as the valve 70, could be controlled by timing mechanisms according to predetermined time schedules.

As can be seen from the foregoing detailed description, this invention provides an improved sample preparation method and apparatus which reduce the sample preparation time far below the preparation times required by the methods and apparatus previously known for the preparation of such samples, with corresponding increases in the sample preparation rate. Consequently, a technician using this system can prepare a much greater number of samples in any given work period, thereby improving the efficiency and reducing the cost of such preparation procedures. This invention significantly increases the efficiency of the isotope recovery from the starting material, permitting recoveries of essentially 100% of the isotope present in the starting material. As a result, the memory of the sample preparation equipment is virtually eliminated, so that the reliability of the resultant samples and the data derived therefrom are greatly improved. The invention also permits the preparation of samples which contain little or no oxygen, thereby minimizing quenching effects. The improved heat exchanger used to recover the condensable vapors provides an extremely high heat transfer with only a small volume and surface area and in a very short time period, and the improved reaction column achieves a high reaction rate between the gas and liquid for the recovery of isotopes to be reacted in gas form with a liquid trapping agent.

I claim as my invention:

1. A method of preparing isotope-containing samples for use in studies utilizing radioactive isotopes, said method comprising the steps of
   a. combusting a sample of material containing the isotope tritium in a combustion chamber to produce combustion products containing tritiated water vapor,
   b. continuously exhausting the tritiated water vapor from said combustion chamber during the combustion of said material,
   c. continuously cooling the exhausted combustion products in a heat exchanger to convert the tritiated water vapor to a liquid during the combustion of said material,
   d. continuously removing said isotope-containing liquid from said heat exchanger during the combustion of said material and transferring said liquid to a sample collection vessel to provide a liquid sample containing the recovered isotope for use in studies utilizing radioactive isotopes,
   e. and purging said combustion chamber and heat exchanger between the combustion of successive isotope-containing samples.

2. A method of preparing samples as set forth in claim 1 wherein said exhausting, cooling, and removing steps are continued after completion of the burning of the sample material until substantially all the $^3H_2O$ is recovered.

3. A method of preparing samples as set forth in claim 1 which includes the step of flushing said combustion chamber with a fluid subsequent to the burning step so as to sweep any residual combustion products out of said chamber and on through said heat exchanger to achieve substantially complete recovery of the $^3H_2O$ while purging the system prior to combustion of the next sample.

4. A method as set forth in claim 1 further characterized by the step of collecting the liquid removed from said heat exchanger in a sample vial attached to the exit of the heat exchanger and directing inert gas from said heat exchanger into said vial so that any oxygen contained in the vial headspace may be displaced to the atmosphere when the vial is removed from the heat exchanger.

5. A method as set forth in claim 1 further characterized by the step of pre-heating the walls of the combustion chamber prior to said burning step so as to maintain said walls above the condensation temperature of the vapors contained in the combustion products.

6. A method as set forth in claim 1 further characterized by the step of maintaining said combustion products above the condensation temperature of the vapors contained therein until said combustion products are cooled in said heat exchanger.

7. A method as set forth in claim 1 further characterized by the step of supplying a liquid to the inlet end of said heat exchanger subsequent to the burning step so that said liquid flows through the heat exchanger to recover any condensed vapors remaining therein.

8. A method as set forth in claim 7 further characterized in that said liquid is a liquid scintillator.

9. A method as set forth in claim 7 further characterized in that said liquid is a solvent for the condensed vapors.

10. A method as set forth in claim 7 further characterized in that a liquid scintillator and a liquid solvent are supplied sequentially to the inlet end of said heat exchanger 11. A method of preparing isotope-containing samples for use in studies utilizing radioactive isotopes, said method comprising the steps of
   a. combusting a sample of material containing a radioactive isotope in a combustion chamber to produce combustion products containing the radioactive isotope in the form of a gaseous product containing tritiated water vapor, said combustion chamber having side walls extending upwardly and inwardly above said sample of material so as to approximate the shape of the flame of a burning sample to minimize the oxygen-containing atmosphere around the flame,
   b. continuously exhausting said isotope-containing combustion products from said combustion chamber during the combustion of said material,
   c. continuously cooling the exhausted combustion products in a heat exchanger to condense any tritiated water vapor and other vapors contained therein during the combustion of said material,
   d. continuously separating the condensed isotope-containing vapors from the remaining gaseous combustion products during the combustion of said material and transferring the condensed vapors to a sample collection vessel to provide a liquid sample containing the recovered isotope for use in studies utilizing radioactive isotopes,
   e. and purging said combustion chamber and heat exchanger between the combustion of successive isotope-containing samples.

12. A method of preparing samples as set forth in claim 11 wherein said exhausting, cooling, and separating steps are continued after completion of the burning of the sample material until substantially all the combustion products are removed from said combustion chamber.

13. A method of preparing samples as set forth in claim 12 which includes the step of flushing said combustion chamber with a fluid subsequent to the burning step so as to sweep any residual combustion products out of said chamber and on through said heat exchanger to achieve substantially complete recovery of the isotope while purging the system prior to combustion of the next sample.

14. A method as set forth in claim 11 wherein said heat exchanger comprises a tube made of thermally conductive material and forming an elongated fluid passageway designed to provide laminar flow of gases and vapors passing therethrough in the absence of condensation, the cross section of said passageway being sufficiently small in at least one direction transverse to the fluid flow to provide a pulsating fluid pressure at the inlet end of said passageway in the presence of condensation therein, the walls of said passageway being maintained at a temperature at least as low as the condensation temperature of the vapors passing therethrough.

15. A method of preparing isotope-containing samples for use in studies utilizing radioactive isotopes, said method comprising the steps of
   a. combusting a sample of material containing a radioactive isotope in a combustion chamber to produce combustion products containing the radioactive isotope in the form of a gaseous product containing tritiated water vapor,
   b. continuously exhausting said isotope-containing combustion products from said combustion chamber during the combustion of said material,
   c. continuously cooling the exhausted combustion products in a heat exchanger to condense any tritiated water vapor and other vapors contained therein during the combustion of said material, said heat exchanger comprising a tube made of thermally conductive material and forming an elongated fluid passageway designed to provide laminar flow of gases and vapors passing therethrough in the absence of condensation, the cross section of said passageway being sufficiently small in at least one direction transverse to the fluid flow to provide a pulsating fluid pressure at the inlet end of said passageway in the presence of condensation therein, the walls of said passageway being maintained at a temperature at least as low as the condensation temperature of the vapors passing therethrough,
   d. continuously separating the condensed isotope-containing vapors from the remaining gaseous combustion products during the combustion of said material and transferring the condensed vapors to a sample collection vessel to provide a liquid sample containing the recovered isotope for use in studies utilizing radioactive isotopes,
   e. and purging said combustion chamber and heat exchanger between the combustion of successive isotope-containing samples.

16. A method of preparing samples as set forth in claim 15 wherein said exhausting, cooling, and separating steps are continued after completion of the burning of the sample material until substantially all the combustion products are removed from said combustion chamber.

17. A method of preparing samples as set forth in claim 16 which includes the step of flushing said combustion chamber and said heat exchanger with a fluid subsequent to the burning step to achieve substantially complete recovery of the isotope while purging the system prior to combustion of the next sample.

* * * * *